United States Patent
Hepper et al.

(10) Patent No.: US 10,512,558 B2
(45) Date of Patent: Dec. 24, 2019

(54) ORTHOSIS AND METHOD FOR PRODUCING SUCH AN ORTHOSIS

(71) Applicant: SPRINGER AKTIV AG, Berlin, OT (DE)

(72) Inventors: Martin Hepper, Berlin (DE); Eric Schreiter, Dortmund (DE)

(73) Assignee: SPRINGER AKTIV AG, Berlin (DE)

( * ) Notice: Subject to any disclaimer, the term of this patent is extended or adjusted under 35 U.S.C. 154(b) by 681 days.

(21) Appl. No.: 15/214,491

(22) Filed: Jul. 20, 2016

(65) Prior Publication Data
US 2017/0020706 A1    Jan. 26, 2017

(30) Foreign Application Priority Data
Jul. 21, 2015   (DE) .................. 10 2015 009 279

(51) Int. Cl.
| | |
|---|---|
| A61F 5/01 | (2006.01) |
| A43B 17/00 | (2006.01) |
| A43B 17/14 | (2006.01) |
| A61F 5/14 | (2006.01) |

(52) U.S. Cl.
CPC .......... *A61F 5/0111* (2013.01); *A43B 17/006* (2013.01); *A43B 17/14* (2013.01); *A61F 5/0127* (2013.01); *A61F 5/14* (2013.01)

(58) Field of Classification Search
CPC .... A61F 5/0111; A61F 5/0113; A61F 5/0127; A61F 5/0195; A61F 5/14; A43B 7/28; A43B 7/30; A43B 13/12; A43B 13/122; A43B 17/00; A43B 17/003; A43B 17/006; A43B 17/02; A43B 17/14; A43B 17/18
See application file for complete search history.

(56) References Cited

U.S. PATENT DOCUMENTS

| | | | | |
|---|---|---|---|---|
| 909,138 | A |   | 1/1909 | Belonga |
| 2,589,241 | A | * | 3/1952 | Galhouse .................. A61F 5/14 12/146 M |
| 2,961,714 | A | * | 11/1960 | Murray .................... A43B 7/28 12/142 N |
| 2,973,529 | A | * | 3/1961 | Silverman ................ A43B 7/28 12/142 N |
| 4,603,024 | A | * | 7/1986 | Denis ....................... A43B 7/28 156/212 |

(Continued)

FOREIGN PATENT DOCUMENTS

WO    2006055474    5/2006

*Primary Examiner* — Kari K Rodriquez
(74) *Attorney, Agent, or Firm* — Mark David Torche; Patwrite Law

(57) ABSTRACT

An orthesis with a foot part and a lower leg part connected with the foot part is characterized in that the foot part comprises an outer shell connected with the lower leg part and an insole arranged inside the outer shell and forming a negative shape of a foot sole; a method for producing such an orthesis includes generating a sole print of patient foot producing an insole matching the sole print; generating a negative shape forming the foot including the insole and lower leg section to be enclosed by the orthesis; generating a positive shape of the foot and lower leg section to be enclosed by the orthesis by filling the negative shape; generating the lower leg part and the outer shell, using the positive shape and the insole as a mould core; and inserting the insole into the outer shell of the foot part.

4 Claims, 4 Drawing Sheets

(56) References Cited

U.S. PATENT DOCUMENTS

Figure 1:
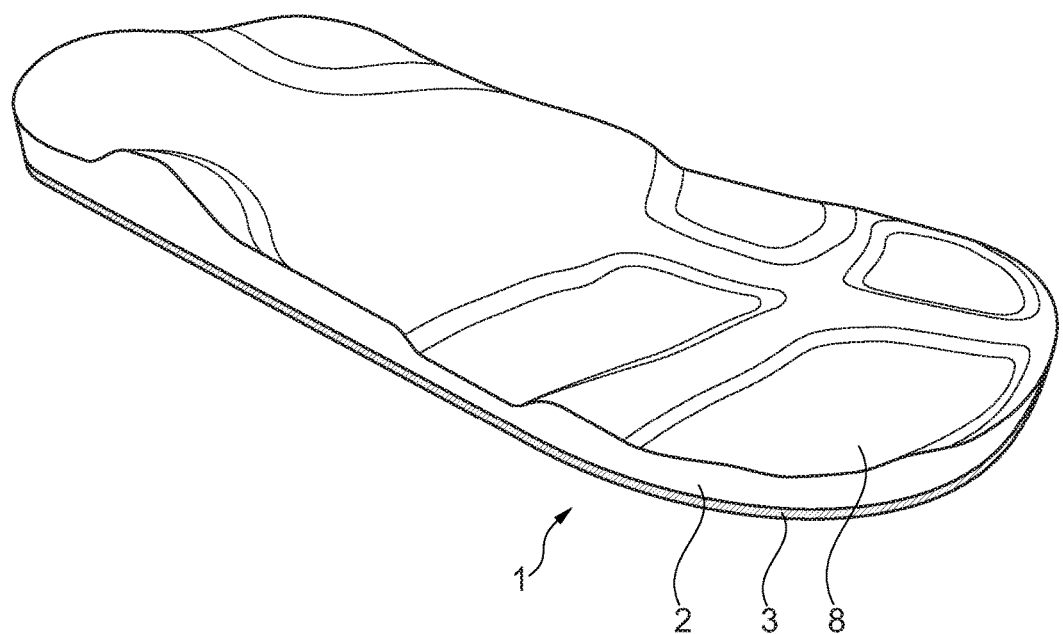

| | | | |
|---|---|---|---|
| 4,868,945 A * | 9/1989 | DeBettignies | A43B 7/28 12/142 N |
| 5,154,173 A * | 10/1992 | Aultman | A43B 7/14 128/DIG. 21 |
| 6,334,854 B1 | 1/2002 | Davis | |
| 6,346,210 B1 | 2/2002 | Swartz et al. | |
| 2004/0194348 A1 | 10/2004 | Campbell et al. | |
| 2005/0038363 A1 | 2/2005 | Stano | |
| 2005/0096576 A1* | 5/2005 | Castro | A61F 5/0127 602/27 |
| 2006/0015050 A1* | 1/2006 | Bleau | A43B 7/141 602/28 |
| 2009/0044426 A1* | 2/2009 | Levine | A43B 7/28 36/88 |
| 2012/0238928 A1* | 9/2012 | Buethorn | A61F 5/0111 602/27 |
| 2014/0066829 A1 | 3/2014 | Drillio | |

* cited by examiner

ORTHOSIS AND METHOD FOR PRODUCING SUCH AN ORTHOSIS

The invention concerns an orthesis with a foot part and a lower leg part as well as a method for producing such an orthesis.

An orthesis is a medical and specifically orthopaedic aid enclosing part of a body, which is used for stabilising, easing, immobilisation, guiding or correcting limbs or the body of a patient depending on the medical indication. An orthesis is produced individually or industrially pre-fabricated or by an orthopaedic technician or orthopaedic shoe technician according to a medical prescription or following private instruction.

A normal method for producing an orthesis with a foot part and a lower leg part can include the following method steps:

Generation of a sole print, a blueprint or a scan of a foot of a patient. This serves for the subsequent production of an orthesis as well as for legally stipulated documentation.

Generation of a so-called foot board, to be used for the subsequent production of a plaster cast. For this the foot board is equipped with relatively large-sized recesses that serve for receiving the prominent bone of the foot in the area of the sole of the foot.

Generation of a plaster negative through circular wrapping of the leg with plaster bandages or longuettes.

Generation of a negative shape of the foot and the section of the lower leg to be enclosed by the orthesis from plaster, wherein so-called plaster truss pads are created on the foot board for forming plaster sole, in which the anatomical sole shape of the foot is replicated exactly. The remaining sections of the negative shape are however generated with plaster bandages that are wrapped around the foot, the foot board and the relevant section of the lower leg.

Generation of a positive shape of the foot and the relevant section of the lower leg through filling the negative shape with plaster. The use of a plaster demoulding cream prevents a connection between the negative shape and the positive shape.

Generation of the orthesis, for example by deep-drawing heated plastic plates, wherein the positive shape is used as a mould core.

The orthesis can then be adjusted with regard to the outer edge shape and equipped with closure elements, for example Velcro.

It is clear that the production of such an orthesis is relatively complex. This is particularly the case with the foot part. One disadvantage of an orthesis produced with such a method is also that the sole shape cannot be changed, or only with extensive effort following its production. This is however necessary in many cases, as it is important for the comfort of a user of such an orthesis that the sole of the orthesis that is on occasion dynamically subjected to a multiple of the body weight should be adapted to the shape of the sole of the foot of the user as precisely as possible in order to prevent pressure points. Readjustments are therefore often required, in particular due to growth when treating children.

Based on this prior art it was the task of the invention to provide an improved orthesis comprising a foot part and a lower leg part. The improved orthesis should in particular enable a simple production and/or a simple adjustment of the inside of the sole following production.

This task is solved by means of an orthesis according to patent claim 1 as well as by means of a method for producing such an orthesis according to patent claim 8. Advantageous designs of such an orthesis and advantageous embodiments of the production method of the invention are the subject of the further patent claims and result from the following description of the invention.

A generic orthesis with a foot part and a lower leg part connected with the foot part is characterised according to the invention in that the foot part comprises an outer shell connected with the lower leg part as well as an insole arranged inside the outer shell and forming a negative shape of a sole of a foot (which is thus formed as a separate element).

A method for producing such an orthesis can advantageously include the following steps:

Generation of a sole print of a foot of a patient.

Production of an insole matched to the sole print. This can for example be realised through machining, and in particular through milling at least the side forming the negative shape of the sole print.

Generation of a negative shape forming the foot including the insole as well as the section of the lower leg to be enclosed by the orthesis. Unlike with the known method the sole print is therefore not only used for diagnosis and/or or documentation purposes with a method according to the invention, but crucially also for forming the sole or at least the inside of the sole of the orthesis. In this way the particularly complex method steps of a conventional method, which serve for generating an individualised plaster sole (including the generation of the foot board) are avoided.

Generation of a positive shape of the foot and the section of the lower leg to be enclosed by the orthesis by filling the negative shape. This can in particular be realised by filling the same with a flowable, curable material such as for example plaster.

Generation of the lower leg part and the outer shell, using the positive shape (once it has been cured) and the insole as a (two-part) mould core. This can preferably be realised through deep-drawing a plastically deformable and then curable blank, for example a heated plate or a block of plastic (for example PE, PP, PET, PPTA, CFC and/or GRP). A generation of the lower leg part and the outer shell can also be realised through applying and curing pre-pegs, i.e. textile pre-products pre-impregnated with reaction resins that are cured under the influence of temperature and/or pressure. A combination of both production variants for the lower leg part and the outer shell is also possible, so that pre-pegs can for example be applied on the outside as additional reinforcement to a base body produced through deep-drawing (preferably with relatively thin walls).

Insertion of the insole into the outer shell of the foot part. The insole is therefore not only used for generating a shell body enclosing the lower leg part and the outer shell of the foot part, but also represents a part of the orthesis itself.

The production method according to the invention is less complex thanks to the said characteristics and advantages.

In a preferred embodiment of an orthesis according to the invention it can be envisaged that the insole is removably arranged in the outer shell. In addition to the method according to the invention it can be envisaged that a disconnectable connection is formed between these components during or after inserting the insole into the outer shell of the foot part. One particularly relevant advantage of a removable arrangement of the insole in the outer shell of the foot part compared to an also possible, (not non-destructive) removal is that a subsequent adjustment of the insole, in particular with regard to the shape of the inside of the sole, can be realised following production, and in particular after prior use (possibly following a first fitting and/or trial phase) by the use. This subsequent adjustment is comparatively easy thanks to the handling of the insole that is separate from the rest of the orthesis.

Another particular advantage is that the insole can be sanitised and cleaned by the possibility of manually removing the same from the orthesis. This substantially improves the hygienic aspect.

Accordingly it can advantageously also be envisaged as part of a method according to the invention that the insole is removed from the foot part by the intended user and revised separately following a fitting of the orthesis. A further advantage is that the insole can be used separately (i.e. without the rest of the orthesis, for example in a shoe) once the healing process has progressed satisfactory and the physician prescribes this as an alternative.

In one preferred design of the orthesis according to the invention it can be envisaged that the insole is made from a material that is dimensionally stable up to a temperature of at least 180° C., preferably up to a temperature of at least 200° C., and more preferably up to a temperature of at least 220° C. in at least one section, and in particular in at least one layer, which preferably extends across the entire main surface of the insole. In this way it can in particular be prevented that a shape change of the insole during production of the orthesis occurs as part of a method according to the invention. This applies in particular for a generation of the lower leg part and the outer shell of the foot part through deep-drawing, where the insole can be exposed to a correspondingly higher temperature. Relatively high temperatures can however also occur during the curing of pre-pegs (for example curing at 130° C. over a period of approx. three hours or at 80° C. over a period of approx. five hours).

It can particularly preferably be envisaged that the insole is made of a mixed material comprising cork (in particular from the rind of the cork oak) in at least one section, and in particular in at least one layer that preferably extends across the entire main surface of the insole. In addition to an adequate thermal dimensional stability the advantages of the respective use of cork, which in particular have a positive influence on producibility as part of a method according to the invention, are high elasticity, which buffers shocks during the use of the orthesis, good air permeability, which reduces transpiration in the orthesis, and low heat conductivity, which can also positively influence comfort during use of the orthesis, as a chilling of the foot during use at low outside temperatures can be avoided.

It can also be particularly preferably be envisaged that the insole consists of a mixed material comprising calcium carbonate (chalk) and/or kaolin and/or ethylene vinyl acetate and/or low-density polyethylene (PE-LD), in particular Bralen, in addition to cork, in at least one section. Kaolin can in particular have a positive influence on the flexibility of the insole, whilst ethylene vinyl acetate and Bralen has a positive influence on elasticity. Calcium carbonate can in turn act positively on the thermal dimensional stability of the mixed material or the insole made from the same.

It can further be preferably envisaged that the section made from the thermally dimensionally stable material and in particular from the mixed material containing cork and/or the further components, is combined with a support layer made from a relatively (compared with the thermally dimensionally stable material and in particular the mixed material and/or the further components) rigid material on the side of the sole of the foot facing away from the negative shape. The support layer can here also preferably extend across the entire main surface of the insole. The support layer can serve for stabilising the insole, in particular during the process step of generating a negative shape of the foot and the section of the lower leg to be enclosed by the orthesis, which can positively influence the quality of the negative shape produced.

The section of made from the thermally dimensionally stable material, and in particular from the mixed material including cork and/or the further components, can further advantageously be combined with a functional layer, for example made from a padding material and/or transpiration inhibiting material, on the side forming the negative shape of the sole of the foot. Such a functional layer can in particular improve the comfort of a user during use of the orthesis. It can also be envisaged as part of a method according to the invention for producing an orthesis according to the invention that the padding layer is applied to the section, and in particular to the layer made of thermally dimensionally stable material, and in particular of the mixed material including cork and/or the further components, as a mould core, soonest after generating the lower leg part and the outer shell of the foot part, using the positive shape and the insole. This can in particular be of advantage when the material of the functional layer is not resilient with regard to temperatures that the insole is subjected to as part of this method step.

The lower leg part and/or the outer shell of the foot part can advantageously be made from PE (polyethylene), PP (polypropylene) and/or PET (polyethylene terephthalate). Also advantageously possible is the use of CFC (carbon fibre-reinforced plastic), GFC (glass fibre-reinforced plastic) and of PPTA (aramide), in particular in the form of plastic reinforced with PPTA fibres. This can make it possible that the lower leg and/or the outer shell of the foot part can be produced with relatively thin walls without an accompanying instability of the orthesis. The weight of the orthesis can in particular be kept low in this way.

The insole can preferably have a proprioceptive mode of action, i.e. hypertonic muscles are inhibited by extending the path between edge and source, and hypotonic muscles are activated by shortening the path between edge and source. The toe bridge and the retro-truss pad can in particular inhibit the plantar flexor muscle groups (Achilles tendon), the lateral longitudinal arch can activate the M. fibularis longus/M. fubularis brevis, and the medial longitudinal arch can activate the M. tibialis anterior.

Alternatively it can also be an insole with a mode of action as first described by Nancy Hylton. A biomechanical stabilisation of the foot is here realised by means of an upright stirrup, so that the afferent nerve paths can provide an improved depth sensitivity to the central nervous system by compressing the foot further, whilst the stability gain generated a tone reaction, the foot is held in a low-reflex position, giving limited freedom in the upper ankle joint. It is of particular advantage if the rear foot points of the heel support on the inside and outside heel are of the same height.

Advantages become obvious in particular here during a comparative examination of orthesis, insole and the foot. An improved depth sensitivity can for example be realised by compressing by means of the PP shell. A corrected shape of the PP shell can generate an upright stirrup (in connection with longitudinal arch modules) and can generate stability gain, which leads to a tone reduction with regard to a low-reflex position. Lowering the ball of the big tor can provide additional support for the front of the foot by means of a position adjustment, which leads to improved support through pressure distribution. Better control of the movement sequence is also possible by means of read foot stabilisation by providing support in the medial and lateral longitudinal arch.

The indefinite [German] articles ("ein", "eine", "einer" and "cities" [all "a" in English]), in particular in the patent claims and in the general explanatory description of the patent claims should be understood as such and not a numerals. Components referred to with the same should therefore be understood as that these can be present at least once, and can be present several times.

Figure 2:
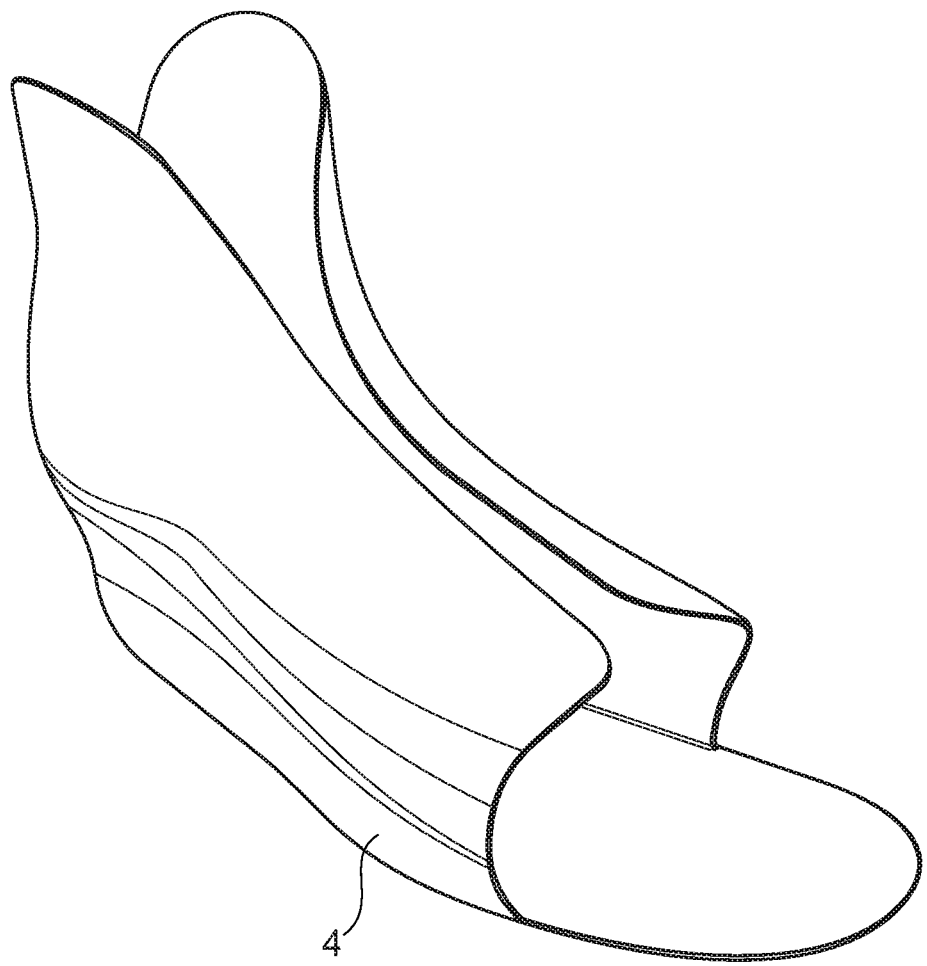
Figure 3:
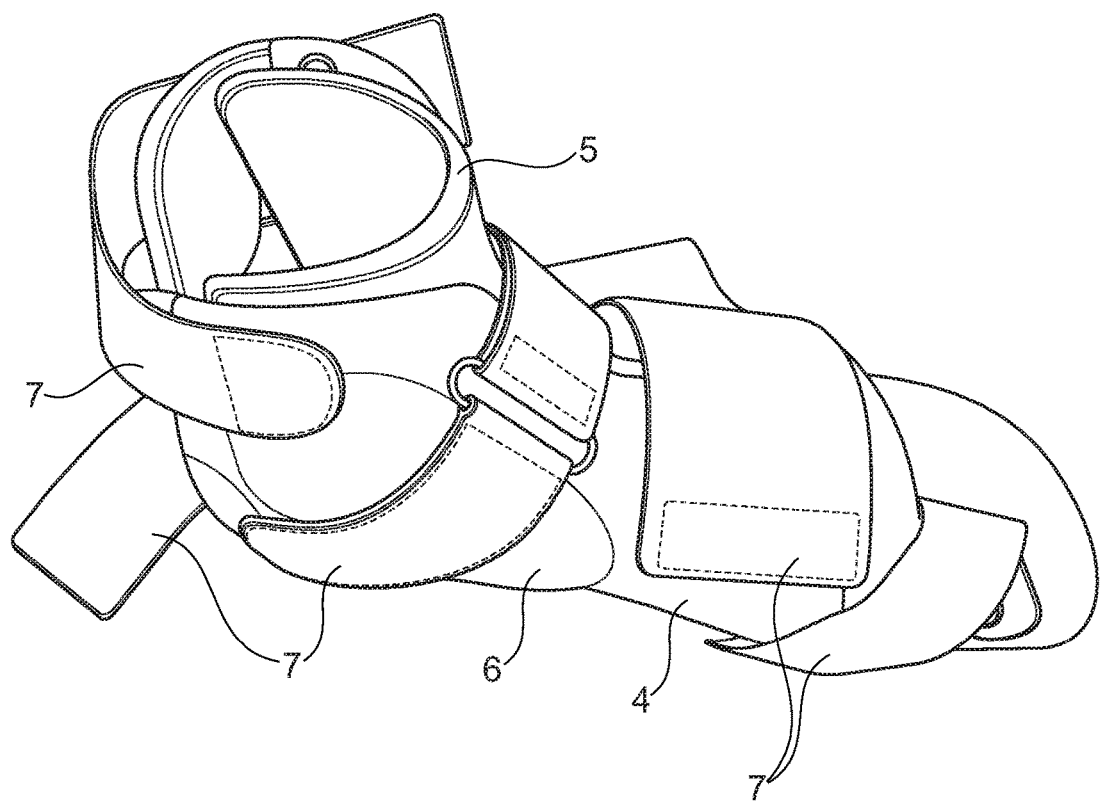
Figure 4:
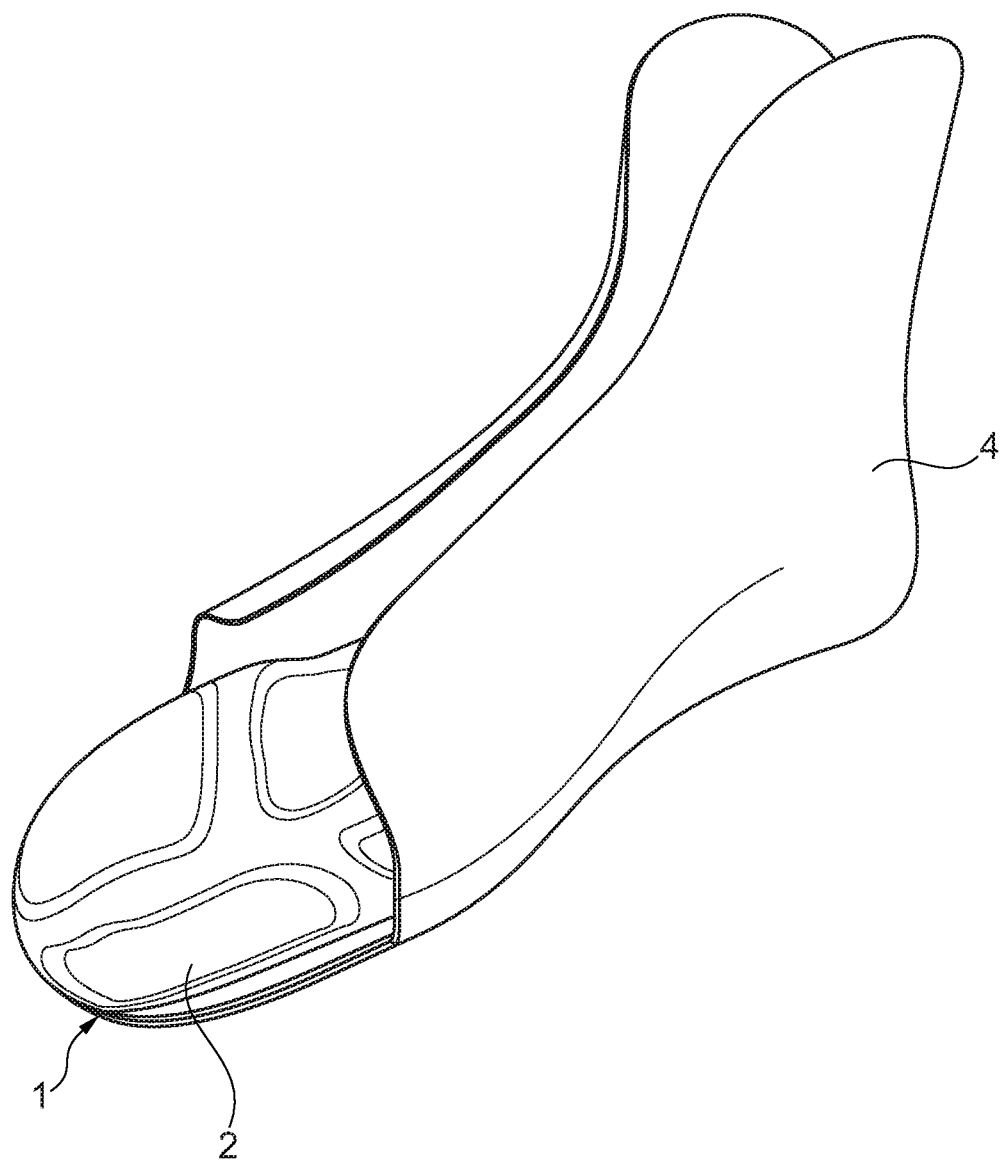

The invention will now be explained in more detail as part of the description of specific embodiments of the method according to the invention with reference to the drawings. The drawings show the orthesis produced with such a method or individual components of the same. In detail the drawings shown in FIG. 1: an insole of an orthesis according to the invention;

FIG. 2: a shell body consisting of the lower leg part and the outer shell of the foot part of an orthesis according to the invention;

FIG. 3: the shell body according to FIG. 2 with additional integrated padding and closure elements; and FIG. 4: an orthesis according to the invention.

In one embodiment of a method according to the invention an order form is first completed on the basis of a case history of a patient, wherein information regarding the indication, the outer appearance and other crucial information for production are included amongst other things.

A sole print of the foot of the patient for which the orthesis is to be produced is also created. This can for example be realised by means of a foam print, a 2D or 3D scan, or also a blueprint. The sole print serves firstly for the completion of statutory documentation, and secondly for producing an insole 1 matched to the sole print (see FIGS. 1 and 4).

The production of this insole 1, or at least a main layer of the same, can for example be realised through machining from a material blank made of sufficiently thermally dimensionally stable material, for example of a mixed material including cork and/or further components. A CNC milling machine enabling a cost effective and precise production of the insole 1 in a short time can be used here. Reproducibility is given.

The insole 1, or the main layer 2 of the insole 1 made from the thermally dimensionally stable material can be combined with a support layer 3, which can for example have a thickness of approximately 2 mm and for example be made from PP. The support layer 3 can here be permanently connected with the main layer 2 or unconnected from the same. The support layer 3 serves for stabilising the insole 1 during the subsequent production of a negative shape of the foot including the insole 1 and the section of the lower leg to be enclosed by the orthesis by means of a plaster cast.

Such a negative shape of the foot including the insole 1 is then generated by means of a plaster cast. This can initially include a control of the module positioning, the tone and the position of the insole 1 on the foot. If necessary the insole 1 can be reworked, wherein the width of the insole 1 in particular can be adapted to the foot. It can be particularly relevant here that the insole 1 is not too narrow in the area of the heel in order to be suitable for a subsequent fitting of a heel cap. If necessary a correction of the surface profile of the insole 1 can also be carried out, wherein corrective wedges can be used if required. This is followed by a greasing of the foot and the relevant section of the lower leg with a plaster demoulding cream, which prevents an excessive adhesion of the plaster to the skin.

The heel cap is then first formed as part of the negative shape. For this the foot is placed on the insole 1 and the calcaneus enclosed with an elongated piece of plaster from the longitudinal arch to the peroneal arch.

The foot is then for example fixed to the insole 1 previously connected with the heel cap with fixing tape (for example adhesive tape). This is carried out depending on previously determined medical indications: for a talipes valgus and/or a sunken pes cavus a supination traction direction is primarily envisaged, whilst a pronation traction direction would more likely be envisaged for a pes cavus and/or a clump foot. Prominent points and in particular the knuckles can for example be marked with indelible pencil.

Soaked plaster bandages are then wrapped around the foot and the insole 1 positioned under the foot as well as around the relevant section of the lower leg for producing the negative shape. It may be useful here to adhere to an inhibited position of the limbs at an angle of approx. 90° whilst applying the plaster bandages.

Once the plaster bandages have hardened, which will take approx. five minutes, the negative shape can be removed from the foot and the lower leg of the patient.

The negative shape included the insole 1 can then be processed, wherein the fixing tape previously affixed to the insole 1 for fixing the same to the foot in particular can be removed and a plaster demoulding cream applied to the inside of the negative shape.

The negative shape is now filled with plaster for producing a positive shape of the foot and the section of the lower leg to be enclosed by the orthesis. Once this has dried this positive plaster shape including the insole 1 can be separated from the negative shape.

Modelling work can then be carried out. The lower leg part and the foot bed of the positive shape in particular can be adjusted to size and the shape of the insole 1 adjusted. Circumference and width measurements can also be checked.

A subsequent method step represents the production of the lower leg part and the outer shell of the foot part, using the positive shape and the insole 1 as the mould core. Producing these integral shell bodies 4 is realised through deep-drawing a heated plastic plate. A 2 mm or 3 mm thick plastic plate made of PP can for example be used to produce an for an orthesis for a child, whilst a 5 mm thick plastic plate made of thermoplastic copolymer (PETG), for example supplied by SIMONA AG under the tradename SIMLOUX, can for example be used for an orthesis for an adult. For this the insole 1 is first cleaned. If necessary a clamping strap 5 and ankle pads 6 can also be affixed to the positive plaster shape. The width of the insole 1 can also be adjusted further. For this an inner sole cutting can be envisaged, where greater flexibility with regard to high pressure in the orthesis, for example caused by growth of the foot or an imprecise circumference modelling of the plaster, can be guaranteed by grinding the insole inner sole (planar side of the insole).

It can then be envisaged to laminate a so-called "dummy", which can be used for the later production of a separate dock and for cutting open the shell unit 4 of the orthesis yet to be produced (see FIGS. 2 to 4).

Deep-drawing thermo-forming then follows, wherein the heated plastic plate is formed under plastic deformation around the unit consisting of the positive shape, insole 1, and possibly the clamping strip 5 (or a corresponding sufficiently thermally dimensionally stable dummy) as well as the ankle pads 6 (or a corresponding sufficiently thermally dimensionally stable dummy). Possible process temperatures can here lie between 160° C. and 180° C. when using PE for the shell unit 4, between 180° C. and 200° C. for the use of PP for the shell unit 4, and between 200° C. and 220° C. if PET is used for the shell unit 4.

The outer edge shape of the shell unit 4 enclosing the lower leg part and the outer shell of the foot part can then be adjusted as well as smoothed. FIG. 2 shows a correspondingly designed shell unit 4. Closure elements 7 can also be provisionally fitted to the same. For a subsequent fitting the insole 2, the clamping strap 5 and the ankle pads 6 can also be provisionally fixed on the shell unit 4 (see FIG. 3, although without insole 1).

During the fitting the module positioning of the insole 1 and its functionality, the volume of the entire orthesis, the heel position and the heel support, in particular with regard to possible pressure points, the position of the closure elements 7 and the edge shape of the orthesis are checked and adjusted if necessary.

A dynamic running analysis can now be carried out with the patient wearing the orthesis. With the aid of the result of this running analysis the inhibition and the stability of the foot and/or the section of the lower leg enclosed by the orthesis can now be changed and optimised, in particular by means of changing the shape of the insole 1. The possibility of removing the insole 1 from the shell unit 4 makes such a revision of the insole 1 easily possible. It can also be envisaged to process the positive shape made of plaster in order to correct pressure points or positioning errors.

After the fitting the desired changed are applied. The ankle pads 6, the clamping strap 5 and possibly soft padding truss pads are glued in, the closure elements 7 sewn on and the shell unit 4 riveted or glued to the same.

It can also be envisaged to cover the insole 1, for example on the side forming the negative shape of the sole of the foot, with a functional layer 8, so that the wearer comfort of the orthesis can be increased. FIG. 1 shows such an insole 1 in an isolated illustration. It may be expedient to envisage a running-in period of, for example, one to two months prior to covering in order not to make a possible revisability of the insole 1 more difficult due to a functional layer 8 that is already permanently integrated into the insole 1.

The insole 1 can then be fitted in the outer shell of the foot part of the orthesis (see FIG. 4). This can for example be realised by using contact adhesive, Velcro in connection with a buddy strap, or double-sided adhesive tape.

Following completion of the orthesis the same can be worn by the patient as required. If necessary, or as part of a check-up, the insole 1 can be removed from the orthesis, which guarantees good control (for example during growth of the patient or if pressure points exist) and very good individual revisability.

A further special advantage is the possibility of a manual removal of the insole from the orthesis, as this can then be sanitised and cleaned. The hygienic aspect is clearly improved.

In one adaptation of the method described above it can be envisaged that the shell unit 4 (as described) is designed with (a) relatively thin wall thickness(es). This then serves as the base body, which can retrospectively be reinforced with a reinforcing layer in the form of a pre-peg, in particular in order to realise sufficient stability.

For this it can be envisaged that the unit consisting of the base body of the shell unit 4 and the positive shape positioned therein, insole 1, possibly the clamping strap 5 (or corresponding dummy) as well as possible ankle pads 6 (or corresponding dummies) are subjected to a vacuum, and the base body then laminated on the outside with, for example, pre-pegs containing carbon fibres and/or aramide fibres. For this, joints may be incorporated into the pre-peg lamination. Sealing by means of a second film can then be envisaged. Underpressure can then be generated between the two films, and thus in the lamination layer. The pre-pegs are now cured. This can for example be realised through heating at underpressure at a temperature of approx. 120° C. or approx. 130° C. over a period of approx. three hours or at a temperature of approx. 80° C. over a period of approx. five hours.

LIST OF REFERENCE NUMBERS

| | |
|---|---|
| 1 | insole |
| 2 | main layer of insole |
| 3 | support layer of insole |
| 4 | shell unit |
| 5 | clamping strap |
| 6 | ankle pad |
| 7 | closure element |
| 8 | functional layer of insole |

The invention claimed is:

1. A method for producing an orthesis with a foot part and a lower leg part connected with the foot part, characterized in that the foot part comprises an outer shell connected with the lower leg part and an insole arranged inside the outer shell and forming a negative shape of a sole of a foot, comprises the steps of:
   a) generating a sole print of a foot of a patient;
   b) producing an insole matching the sole print;
   c) generating a negative shape forming the foot, including the insole and a section of the lower leg part to be enclosed by the orthesis;
   d) generating a positive shape of the foot and the section of the lower leg part to be enclosed by the orthesis by filling the negative shape;
   e) generating the lower leg part and the outer shell, using the positive shape and the insole as a mold core; and
   f) inserting the insole into the outer shell of the foot part.

2. The method according to claim 1, characterized in that the insole is removed from the foot part after a fitting and revised separately.

3. The method according to claim 2, characterized in that the lower leg part and the outer shell of the foot part are produced by means of deep-drawing.

4. The method according to claim 1, characterized in that the lower leg part and the outer shell of the foot part are produced by means of deep-drawing.

* * * * *